(12) United States Patent
Yamamoto et al.

(10) Patent No.: US 9,845,294 B2
(45) Date of Patent: Dec. 19, 2017

(54) RING CLOSING METATHESIS APPROACH TO PRODUCE PRECURSORS OF NYLON 11, 12, AND 13 FROM OLEIC ACID

(71) Applicant: The University of Toledo, Toledo, OH (US)

(72) Inventors: Kana Yamamoto, Toledo, OH (US); Sridhar Viamajala, Toledo, OH (US); Sasidhar Varanasi, Toledo, OH (US); Ajith Yapa Mudiyanselage, Toledo, OH (US); Godwin Ameh Abel, Toledo, OH (US)

(73) Assignee: The University of Toledo, Toledo, OH (US)

( * ) Notice: Subject to any disclaimer, the term of this patent is extended or adjusted under 35 U.S.C. 154(b) by 0 days.

(21) Appl. No.: 15/323,583

(22) PCT Filed: Jul. 2, 2015

(86) PCT No.: PCT/US2015/038976
§ 371 (c)(1),
(2) Date: Jan. 3, 2017

(87) PCT Pub. No.: WO2016/004299
PCT Pub. Date: Jan. 7, 2016

(65) Prior Publication Data
US 2017/0158640 A1    Jun. 8, 2017

Related U.S. Application Data

(60) Provisional application No. 62/020,488, filed on Jul. 3, 2014.

(51) Int. Cl.
*C07D 225/02* (2006.01)

(52) U.S. Cl.
CPC .................. *C07D 225/02* (2013.01)

(58) Field of Classification Search
CPC .................................................... C07D 225/02
See application file for complete search history.

(56) References Cited

FOREIGN PATENT DOCUMENTS

CN        102391417    *   8/2013

* cited by examiner

*Primary Examiner* — Erich A Leeser
(74) *Attorney, Agent, or Firm* — MacMillan, Sobanski & Todd, LLC

(57) ABSTRACT

Provided herein is a method of producing C11, C12, and C13 nylon precursors from oleic acid or esters of oleic acid, the method involving amide formation, ring-closing metathesis, and hydrogenation. Further provided are the products of the method described. Provided herein is a method for producing a lactam, the method comprising the steps of converting oleic acid or an ester of oleic acid into an amide having a general formula of $H_3C-(CH_2)_rCH=CH-(CH_2)_rCONR-(CH_2)_n-CH=CH_2$, wherein n is 1, 2, or 3, and R is either hydrogen or benzyl; subjecting the amide to a ring-closing metathesis reaction to produce an intermediate having a general formula of $-(CH_2)_rCONR-(CH_2)_n-CH=CH_2-$, wherein n is 1, 2, or 3, R is either hydrogen or benzyl, and both ends are connected to each other; and hydrogenating the intermediate to produce a saturated lactam. In certain embodiments, the saturated lactam has a formula of $-NH-(CH_2)_{10}-CO-$.

19 Claims, 15 Drawing Sheets
(14 of 15 Drawing Sheet(s) Filed in Color)

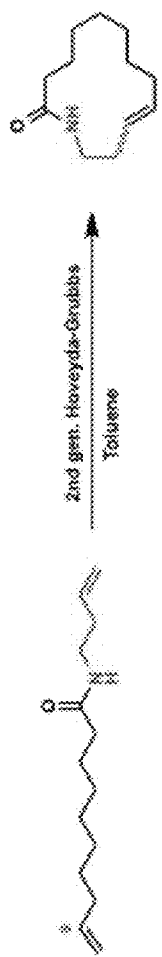
FIG. 9 - Table 1

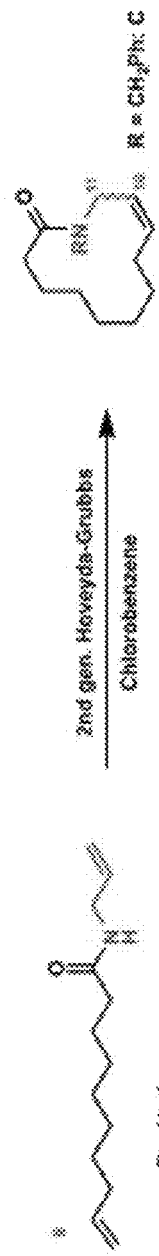
| Entry | Substrate | Conc.(mM) | Cat. (mol%) | Time(h) | Temp. (°C)[f] | C[d][e] | B or A[d] |
|---|---|---|---|---|---|---|---|
| 1 | A | 10 | 1 | 17 | 110 | 0 | 56 |
| 2 | A | 10 | 5 | 6 | 110 | 0 | 31 |
| 3 | A | 4 | 2 | 2 | 110 | 0 | 78 |
| 4 | A | 0.5 | 2 | 6 | 110 | 0 | 30 |
| 5 | A | 4 | 2 | 7 | 110 | 0 | 36 |
| 6 | A | 2 | 5 | 2.5 | 90 | 0 | 78 |
| 7[b] | A | 2 | 2 | 5 | 90 | 0 | 70 |
| 8 | B | 2 | 2 | 2 | 80 | 33.7 | 26.4 |
| 9 | B | 2 | 2 | 2 | 90 | 44.3 | 26.9 |
| 10[c] | B | 2 | 2 | 2 | 90 | 24.8 | 29.8 |
[b] With Ti(OiPr)4 (5 mol%). [c] With Benzoquinone (10 mol%). [d] GC area%. [e] Due to the insufficient peak separation, these numbers are inaccurate. [f] Oil bath temperature.
FIG. 10 - Table 2

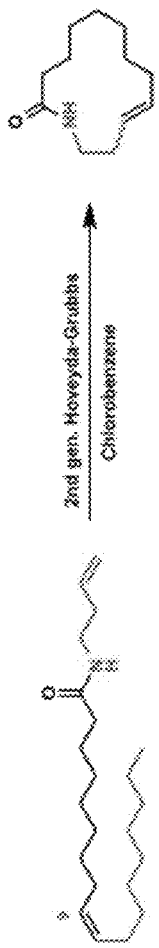
| Entry | Temp. (°C)[a] | Time (min) | Catalyst (mol%) | Conc. (mM) | Conv. (%) | C12 lactam (%)[f] | Oligomers (%)[f] |
|---|---|---|---|---|---|---|---|
| 1 | 90 | 120 | 2 | 2 | 94 | 43.9 | 18.8 |
| 2 | 90 | 60 | 2 | 2 | 92 | 38.8 | 22.1 |
| 3 | 90 | 120 | 2 | 3 | 93 | 45.5 | 9.5 |
| 4[b] | 90 | 60 | 2 | 2 | 97 | 46.6 | 3.8 |
| 5 | 90 | 60 | 2 | 20 | 92 | 18.6 | 22.2 |
| 6 | 90 | 60 | 2 | 10 | 96 | 21.6 | 13.8 |
| 7 | 90 | 60 | 2 | 2 | 97 | 46.8 | 16.3 |
| 8[c] | 90 | 120 | 2 | 2 | 96 | 52.1 | 23.6 |
| 9 | 100 | 60 | 2 | 2 | 95 | 59.6 | 19.6 |
| 10 | 110 | 60 | 2 | 2 | 96 | 64.1 | 16.2 |
| 11 | 120 | 60 | 2 | 2 | 95 | 65.5 | 15.0 |
| 12[b] | 120 | 30 | 2 | 2 | 97 | 71.3 | 10.3 |
| 13[b] | 120 | 15 | 1 | 2 | 96 | 70.2 | 10.6 |
| 14[b] | 120 | 15 | 1 | 4 | 93 | 58.1(87)[d] | 15.0 |
[b] Catalyst added at once. [c] With benzoquinone (10 mol%). [d] Isolated yield. [e] Oil bath temperature. [f] GC area%.
FIG. 11 – Table 3

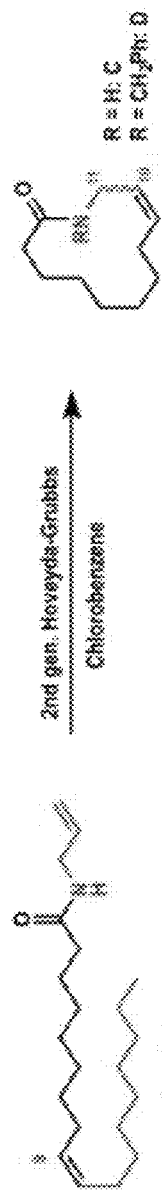
| Entry | Substrate | Conc.(mM) | Cat.(mol%) | Time (h) | Temp.(°C)[a] | C or D[d] | A or B[d] | Oligomers[c] |
|---|---|---|---|---|---|---|---|---|
| 1 | A | 2 | 2 | 22 | 110 | 16 | 60 | 12.3 |
| 2 | B | 2 | 2 | 1 | 110 | 49 (53)[b] | 14 | 10.3 |
| 3 | B | 2 | 2 | 2 | 120 | 57 (53)[b] | 5 | 10.0 |
| 4 | B | 2 | 2 | 2 | 120 | 51 (55)[b] | 9 | 9.7 |
[b] Isolated yield. [c] GC area%.
FIG. 12 – Table 4

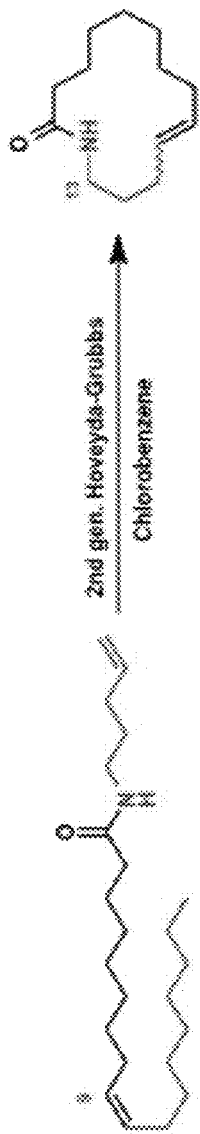
| Entry | Temp. (°C) | Time (min) | Cat. (mol %) | Conc. (mM) | Conv. (%) | C13 lactam[d] | Oligomers[d] |
|---|---|---|---|---|---|---|---|
| 1 | 110 | 120 | 2 | 2 | 92 | 55.5(83)[b] | 20.8 |
| 2[c] | 120 | 15 | 2 | 4 | 93 | 42.7 | 23.5 |
| 3 | 110 | 120 | 1 | 2 | 94 | 49.3 | 21.2 |
| 4 | 110 | 120 | 2 | 0.5 | 95 | 65.7 | 9.5 |
| 5 | 110 | 120 | 2 | 2 | 93 | 47.4 | 14.7 |
| 6 | 90 | 120 | 2 | 2 | 93 | 42.0 | 20.6 |
[b] Isolated yield. [c] Catalyst added at once. [d] GC area%.
FIG. 13 – Table 5

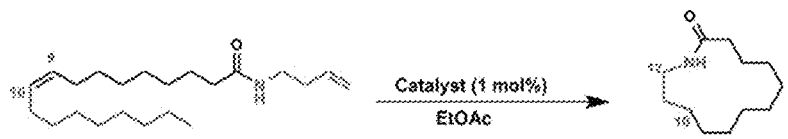

| Entry[a] | Temp. (°C)[b] | Time (min) | Catalyst | Conc. (mM) | Conv. (%)[c] | C12 lactam (%)[c] | Oligomers (%)[c] |
|---|---|---|---|---|---|---|---|
| 1 | 60 | 15 | 1 | 2 | 98 | 55 | 21.05 |
| 2 | 60 | 15 | 3 | 2 | 97 | 54.7 | 20.6 |
| 3 | 60 | 60 | 3 | 2 | 97 | 51 | 22 |
| 4 | 22 | 60 | 3 | 2 | 95 | 31.3 | 37.4 |
| 5 | 60 | 15 | 5 | 2 | 97.4 | 77.4 | 13.4 |
| 6 | 60 | 30 | 5 | 2 | 97 | 72.6 | 21.7 |
| 7 | 60 | 60 | 5 | 2 | 97 | 68.2 | 23.7 |
| 8 | 60 | 15 | 6 | 2 | 93 | 32 | 46 |
| 9 | 60 | 30 | 6 | 2 | 98 | 52 | 36 |
| 10 | 60 | 60 | 6 | 2 | 98 | 74 | 21 |
| 11 | 60 | 15 | 7 | 2 | 98 | 70 | 26.4 |
| 12 | 60 | 60 | 7 | 2 | 97 | 59 | 21 |
| 13 | 22 | 60 | 7 | 2 | 97 | 49 | 40 |
| 14 | 60 | 15 | 8 | 2 | 90 | 66.3 | 17.2 |
| 15 | 60 | 60 | 8 | 2 | 97 | 66 | 19 |
| 16 | 22 | 60 | 8 | 2 | 91 | 30 | 32 |
| 17 | 60 | 30 | 9 | 2 | 97.5 | 63 | 19 |
| 18 | 60 | 60 | 9 | 2 | 95.4 | 59 | 21 |
| 19 | 60 | 240 | 9 | 2 | 96.2 | 55 | 22 |
| 20 | 60 | 15 | 10 | 2 | 96.1 | 49 | 28 |
| 21 | 60 | 30 | 10 | 2 | 97.5 | 60 | 28 |
| 22 | 60 | 60 | 10 | 2 | 97 | 57 | 29 |
| 23 | 60 | 15 | 11 | 2 | 96 | 72 | 17 |
| 24 | 60 | 30 | 11 | 2 | 92 | 56 | 12 |
| 25 | 60 | 60 | 11 | 2 | 92 | 55 | 14 |
| 26[d] | 60 | 15 | 11 | 2 | 98 | 94.4 | 1.8 |
| 27[d] | 60 | 30 | 11 | 2 | 94.3 | 88.1 | 4.3 |
| 28[d] | 60 | 60 | 11 | 2 | 94.2 | 83.3 | 6.6 |
| 29[e] | 60 | 15 | 11 | 2 | 97.6 | 76.9 | 4.5 |
| 30[d,e] | 60 | 15 | 11 | 2 | 95 | 74.7 | 4.0 |
| 31[d,e] | 60 | 15 | 11 | 2 | 71 | 50.2 | 12.5 |
| 32 | 60 | 15 | 13 | 2 | 52.4 | 43.7 | 7.9 |
| 33 | 60 | 30 | 13 | 2 | 54.1 | 42.4 | 8.7 |

[a] Reaction conditions: 1 mol% of the catalyst in EtOAc (1 mL) was added into a solution of the substrate (0.033 mmol) in EtOAc (15 mL) in one portion. The reaction was kept at indicated temperatures before samples were taken for GC analyses. [b] Oil bath temperature. [c] GC area%. [d] Hexanes were used as the solvent. [e] The catalyst immobilized on silica gel was used. [f] The recycled catalyst immobilized on silica gel was used.

FIG. 14

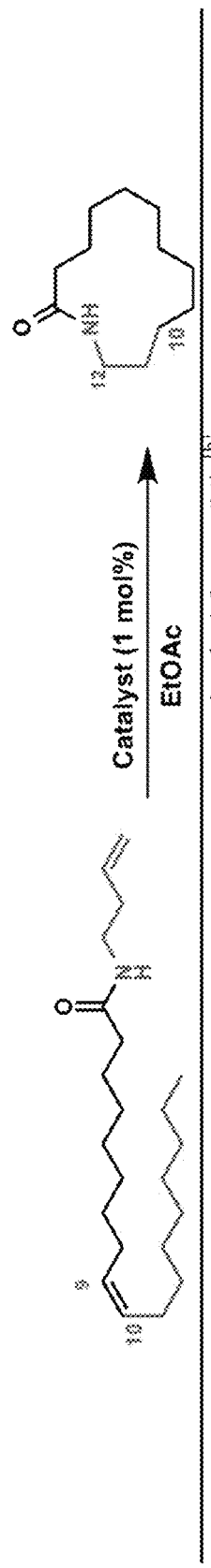
FIG. 15 – Table 7

RING CLOSING METATHESIS APPROACH TO PRODUCE PRECURSORS OF NYLON 11, 12, AND 13 FROM OLEIC ACID

RELATED APPLICATIONS

This application is a national stage application filed under 35 U.S.C. §371 of international application PCT/US15/38976, filed under the authority of the Patent Cooperation Treaty on Jul. 2, 2015, published; which claims priority to U.S. Provisional application No. 62/020,488 filed under 35 U.S.C. §111(b) on Jul. 3, 2014. The entire disclosures of all the aforementioned applications are expressly incorporated herein by reference for all purposes.

STATEMENT REGARDING FEDERALLY SPONSORED RESEARCH

This invention was made with government support under Grant Number CHE-1230609 awarded by the National Science Foundation. The government has certain rights in this invention.

BACKGROUND OF THE INVENTION

Nylon is a series of polymers having the general formula —[$(CH_2)_n$—CONH]— or —[$(CH_2)_n$—CONH—$(CH_2)_m$—NHCO]—, typically named with the length of the methylene units separating the amide functions. Some examples are nylon 6, nylon 7, nylon 8, nylon 9, nylon 11, nylon 12, and nylon 13.

Nylon 11 and nylon 12 in particular possess excellent chemical resistance, thermal resistance, cold impact resistance, flexibility, and durability. There are many industrial applications of these nylons, including automotive, sports, medical, high-performance cables, electronics, electrical materials, and even lenses for glasses. Currently, about 100,000 metric tons of nylon 11 and nylon 12 are produced annually. The use of these nylons in the automotive/transportation industry is increasing at an annual rate of 33.7%, extrapolated to 250,000 metric tons by 2016. Similarly, their use in photovoltaic panels is expected to increase at an annual rate of 36.1% through 2016, and in other general applications is predicted to increase at 25.3% annually through 2016. Nylon 13 has analogous characteristics to nylon 12 and may be used in similar applications as nylon 12.

Nylon 11, 12, and 13 can be produced from amino acids or their derivatives such as esters or lactams (cyclic amide of the amino acid). Currently, the main supply source of C12 amino acid (in lactam form) is from Evonik Industries, of Essen, Germany, which produces this precursor of nylon 12 from petroleum-derived butadiene in a six-step process. While the carbon backbone can be obtained from petrochemical sources by chemical synthesis, there is an increasing interest in the use of renewable resources for production of these amino acids (and their derivatives), due to growing environmental and sustainability concerns. As such, approaches that use natural fatty acids and esters from plant- or algae-derived biomass as the starting materials are attractive. Among the natural fatty acids, oleic acid is the predominant component of lipids in most vegetable oils (e.g., soy oil) and algae.

Conventional approaches to produce 11-aminoundecanoic acid (C11 amino acid) from oleic acid or recinoleic acid (the main component of castor oil)—involve subjecting the acid or ester to a cross metathesis reaction with acrylonitrile to produce 10-cyano-9-decenoic acid or ester, followed by reduction using high-pressure hydrogenation to remove unsaturation. (PRIOR ART FIG. 1, top reaction.) 12-Aminododecanoic acid (C12 amino acid) is also prepared in analogous fashion starting from 10-undecenoic acid prepared from pyrolysis of recinoleic acid. (PRIOR ART FIG. 1, bottom reaction.) It has been stated that α-ω-diacids or diesters can be synthesized by homometathesis or fermentation, or acids or esters with a terminal olefin can be prepared from ethylenolysis as the starting material in lieu of oleic acid. In one method, 10-undecenitrile derived from 10-undecylenic acid derivatives, readily available from recinoleic acid, is subjected to cross metathesis with methyl acrylate, delivering a similar cyano-ester which upon hydrogenation provides C12 amino-esters. 10-Undecenitrile is also subjected to tandem isomerization/hydroformylation and oxidation to access an analogous cyano acid, which can be converted to C12 amino acid.

Finally, another method starts with either 9-decenoic or 10-undecenoic acids or esters (or other ω-terminal fatty acids with various chain lengths) that are subjected to cross-metathesis with either 2-pentenenitrile or 3-pentenenitrile, resulting in unsaturated nitriles or their esters. (PRIOR ART FIG. 2.) This method produces unsaturated nitriles and esters that are then hydrogenated using known methods. Notably, this method produces low yields (between 13-30%) when 3-pentenenitrile is used to produce nylon 12 amino acid. Alternatively, 10-undecenoic acid can be hydrocyanated and then hydrogenated for C12 amino acid production.

There is a need for additional and improved renewable methods of producing nylons, and their precursors, that are simpler, cheaper, and/or involve milder reaction conditions.

SUMMARY OF THE INVENTION

Provided herein is a method for producing a lactam, the method comprising the steps of converting oleic acid or an ester of oleic acid into an amide having a general formula of $H_3C$—$(CH_2)_7$—CH=CH—$(CH_2)_7$—CONR—$(CH_2)_n$—CH=$CH_2$, wherein n is 1, 2, or 3, and R is either hydrogen or benzyl; subjecting the amide to a ring-closing metathesis reaction to produce an intermediate having a general formula of —$(CH_2)_7$—CONR—$(CH_2)_n$—CH=$CH_2$—, wherein n is 1, 2, or 3, R is either hydrogen or benzyl, and both ends are connected to each other; and hydrogenating the intermediate to produce a saturated lactam. In certain embodiments, the saturated lactam has a formula of —NH—$(CH_2)_{10}$—CO—. In certain embodiments, the saturated lactam has a formula of —NH—$(CH_2)_{11}$—CO—. In certain embodiments, the saturated lactam has a formula of —NH—$(CH_2)_{12}$—CO—.

In certain embodiments, the converting comprises subjecting the oleic acid or ester of oleic acid to an amide formation reaction with allyl amine or benzyl allyl amine. In certain embodiments, the converting comprises subjecting the oleic acid or ester of oleic acid to an amide formation reaction with homoallyl amine or benzyl homoallyl amine. In certain embodiments, the converting comprises subjecting the oleic acid or ester of oleic acid to an amide formation reaction with bishomoallyl amine or benzyl bishomoallyl amine.

In certain embodiments, the amide has a formula of $H_3C$—$(CH_2)_7$—CH=CH—$(CH_2)_7$—CONR—$(CH_2)_n$—CH=$CH_2$, where R is either hydrogen or benzyl and n=1, 2 or 3. In certain embodiments, the converting comprises acid chloride formation using oxalyl chloride followed by treatment with an amine. In particular embodiments, the converting is conducted in an amidation solvent selected from the group consisting of: chlorobenzene, triethylamine, toluene, dichloroethane, chloropentafluorobenzene, octafluorotoluene, $CH_2Cl_2$, MeOH, pentane, hexane, heptane, EtOAc, i-ProAc, dimethyl carbonate, diethyl carbonate, HOAc, DMSO, DMF, pyridine, anisole, water, $Et_2O$, acetonitrile, hexafluorobenzene, and mixtures thereof.

In certain embodiments, the intermediate has a formula of $-(CH_2)_7-CONH-(CH_2)_2-CH=CH_2-$. In certain embodiments, the intermediate has a formula of $-(CH_2)_7-CONH-(CH_2)_3-CH=CH_2-$. In certain embodiments, the intermediate has a formula of $-(CH_2)_7-CONR-CH_2-CH=CH_2-$, and R is either hydrogen or benzyl.

In certain embodiments, the ring-closing metathesis reaction is conducted in the presence of a metathesis catalyst. In particular embodiments, the metathesis catalyst comprises a second generation Hoveyda-Grubbs catalyst (FIG. 3, complex 1), Stewart-Grubbs catalyst (FIG. 3, complex 5), or Umicore M7 catalysts such as M74SiPr (FIG. 3, complex 11). In particular embodiments, the metathesis catalyst is attached to a solid support. In particular embodiments, at least one of the amide or the metathesis catalyst is dissolved in a metathesis solvent selected from the group consisting of: chlorobenzene, toluene, dichloroethane, chloropentafluorobenzene, octafluorotoluene, $CH_2Cl_2$, anisole, MeOH, pentane, hexane, heptane, EtOAc, i-ProAc, dimethyl carbonate, diethyl carbonate, HOAc, DMSO, DMF, pyridine, water, $Et_2O$, acetonitrile, hexafluorobenzene, and mixtures thereof. In particular embodiments, the metathesis solvent is selected from the group consisting of chlorobenzene, toluene, EtOAc, and hexane.

In certain embodiments, the ring-closing metathesis reaction is conducted at a metathesis reaction temperature ranging from about 15° C. to about 120° C. In particular embodiments, the metathesis reaction temperature ranges from about 23° C. to about 110° C. In particular embodiments, the ring-closing metathesis reaction is conducted at a metathesis catalyst loading ranging from about 0.1 mol % to about 4 mol %. In particular embodiments, the metathesis catalyst loading ranges from about 1 mol % to about 2 mol %. In certain embodiments, the ring-closing metathesis reaction is conducted at a metathesis reaction concentration ranging from about 0.5 mmol/L to about 4 mmol/L. In particular embodiments, the metathesis reaction concentration is about 2 mmol/L. In certain embodiments, the ring-closing metathesis reaction is conducted with a catalyst addition time of up to about 2 hours. In certain embodiments, the ring-closing metathesis reaction is conducted with a catalyst addition time of up to about 1 hour.

In certain embodiments, the hydrogenation is conducted in the presence of a hydrogenation catalyst. In particular embodiments, the hydrogenation catalyst comprises a complex of Pd, Ru, or Ir. In certain embodiments, the hydrogenation is conducted in a hydrogenation solvent comprising one or more of water, alcohols, ethers, esters, aromatic hydrocarbons, or aliphatic hydrocarbons. In particular embodiments, the hydrogenation solvent is selected from the group consisting of chlorobenzene, toluene, dichloroethane, chloropentafluorobenzene, octafluorotoluene, anisole, $CH_2Cl_2$, MeOH, HCl, pentane, hexane, HOAc, EtOAc, DMSO, DMF, pyridine, water, $Et_2O$, acetonitrile, hexafluorobenzene, chloroform, cyclohexane, ethyl ether, and mixtures thereof. In particular embodiments, the hydrogenation solvent comprises a mixture of MeOH and HCl. In certain embodiments, the hydrogenation is conducted at atmospheric pressure.

In certain embodiments, the method further comprises subjecting the saturated lactam to a ring-opening polymerization process to produce a nylon polymer. In certain embodiments, the method further comprises the steps of subjecting the saturated lactam to a ring-opening reaction to produce a linear nylon precursor, and subjecting the linear nylon precursor to a polymerization process to produce a nylon polymer.

Further provided are the products of the method described herein.

BRIEF DESCRIPTION OF THE DRAWINGS

The patent or application file contains one or more drawings executed in color and/or one or more photographs. Copies of this patent or patent application publication with color drawing(s) and/or photograph(s) will be provided by the U.S. Patent and Trademark Office upon request and payment of the necessary fees.

PRIOR ART

PRIOR ART

FIG. 9: Table 1, describing ring-closing metathesis reaction optimization for C12 ene-lactam formation. Reaction conditions: Hoveyda-Grubbs 2nd generation catalyst in toluene (1 mL) was charged into a solution of the starting material in toluene over 1 h at the stated temperature.

FIG. 10: Table 2, describing ring-closing metathesis reaction optimization for C11 ene-lactam formation. Reaction conditions: Hoveyda-Grubbs 2nd generation catalyst in chlorobenzene was charged into a solution of 9-decinoic acid amide in chlorobenzene over 1 h at the stated temperature.

FIG. 11: Table 3, describing ring-closing metathesis reaction optimization for C12 ene-lactam formation. Reaction conditions: Hoveyda-Grubbs 2nd generation catalyst in chlorobenzene was charged into a solution of oleic acid homoallylamide in chlorobenzene over 1 h at the stated temperature.

FIG. 12: Table 4, describing ring-closing metathesis reaction optimization for C11 ene-lactam formation. Reaction conditions: Hoveyda-Grubbs 2nd generation catalyst in chlorobenzene was charged into a solution of 9-decinoic acid amide in chlorobenzene over 1 h at the stated temperature.

FIG. 13: Table 5, describing ring-closing metathesis reaction optimization for C13 ene-lactam formation. Reaction conditions: Hoveyda-Grubbs 2nd generation catalyst in chlorobenzene was charged into a solution of oleic acid bis-homoallyl amide in chlorobenzene over 1 h at the stated temperature.

FIG. 14: Table 6, describing solvent and catalyst screening directed for optimization of ring-closing metathesis reaction for C12 ene-lactam formation. Reaction conditions: 1 mol % of the catalyst in EtOAc (1 mL) was added into a solution of the substrate (0.033 mmol) in EtOAc (15 mL) in one portion. The reaction was kept at indicated temperatures before samples were taken for GC analyses.

FIG. 15: Table 7, describing catalyst stability evaluation of various metathesis catalysts that provided good reaction conversion and selectivity for the first round under the indicated reaction conditions. Evaluation method: the substrate (0.033 mmol) in 1 mL of EtOAc was added every 15 min to a 15 mL EtOAc solution containing 1 mol % (initial conc.) of the catalyst at 60° C. 1 mL of the solution was taken for GC analyses at 15 min intervals for five times prior to addition of substrate solution.

DETAILED DESCRIPTION OF THE INVENTION

Figure 1:
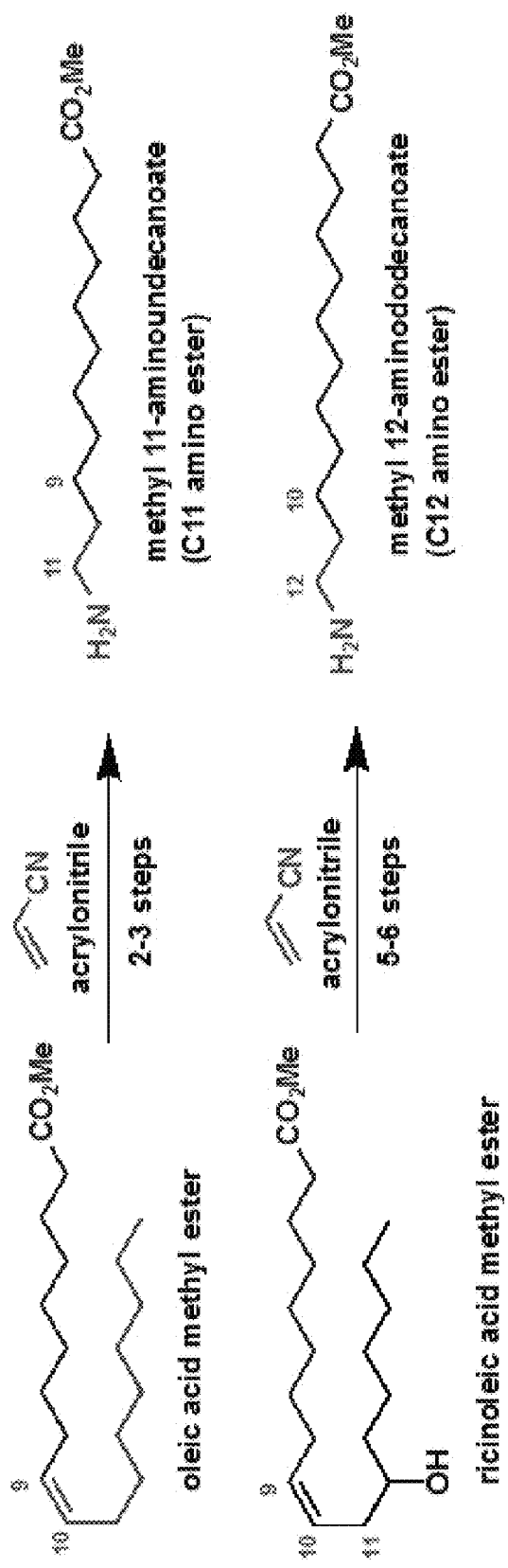
FIG. 1: Schemes showing various known methods of producing C11 and C12 amino esters.
Figure 2:
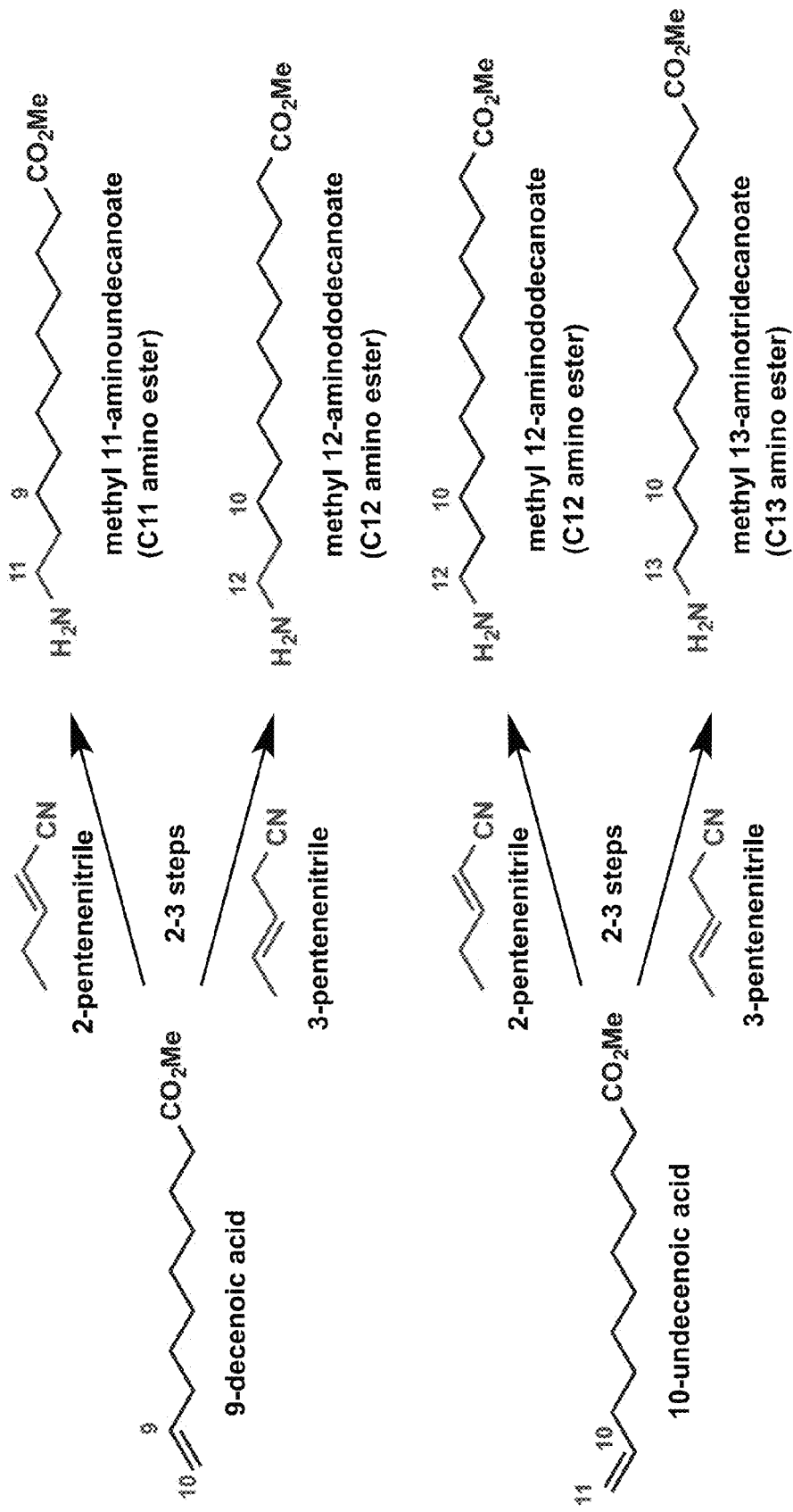
FIG. 2: Schemes showing various known methods of producing C11, C12, and C13 amino esters.

Throughout this disclosure, various publications, patents, and published patent specifications are referenced by an identifying citation. The disclosures of these publications, patents, and published patent specifications are hereby incorporated by reference into the present disclosure in their entirety to more fully describe the state of the art.

Nylons 11, 12, and 13 are produced from amino acids or their derivatives. Nylon 11 precursor has been prepared from oleochemical resources in as short as 3 steps. However, nylon 12 precursor requires at least 5-6 steps from either petrochemical or oleochemical resources. Thus, provided herein is a three-step method for synthesizing precursors of nylon 11, 12, and 13 from unsaturated fatty acids including lipid-rich algae, oleic acid, or any oil that has omega-9 fatty acids as a main component. The three-step method for preparing C11, C12, or C13 lactams from oleic acid or its esters involves a ring-closing metathesis that produces cyclic amides of fatty chain amino acids (lactams). In particular examples, the three-step method synthesizes lactams of 11-aminoundecanoic-, 12-aminododecanoic-, or 13-aminotridecanoic acids from oleic acid or amino esters of oleic acid. The method can use oleic acid originating from vegetable oils or algal lipids.

The method generally involves first preparing allyl, homoallyl, or bishomoallyl amides of oleic acid, with or without nitrogen protection. Then, the amides are subjected to a ring-closing metathesis reaction to form lactam intermediates. Following the ring-closing metathesis, a low-pressure hydrogenation of the lactam intermediates provides the final products. In particular non-limiting examples, the final products can be 2-azacyclododecanone, 2-azacyclotridecanone, or 2-azacyclotetradecanone. This three-step method allows for the direct conversion of oleic acid, which is a widely abundant natural fatty acid, into synthetic precursors of nylon 11, 12, and 13 in a fewer number of steps than previously known methods.

The method described herein has many advantages over other strategies for producing nylon precursors, allowing for the efficient production of these widely used bioplastics. The method allows direct conversion of oleic acid, which is an abundant fatty acid, into synthetic precursors or nylon 11, 12, and 13. The method uses an efficient three-step process: amide preparation, ring-closing metathesis, and low-pressure hydrogenation, as compared to other methods that involve upwards of five steps and use high-pressure hydrogenation. Furthermore, the presently described method is a low-temperature process that provides exceptional conversion and selectivity. A wide variety of catalysts are useful in this method, making the method versatile. In addition, the use of renewable resources from plant-derived biomass is more environmentally friendly than current methods to produce the precursor materials. The ring-closing metathesis method described herein produces fewer undesired by-products and hazardous wastes than current methods. Finally, the feedstock is readily available and non-toxic, as compared to castor oil, which contains ricin.

High yields of the nylon precursors are obtained from oleic acid using the three-step method described herein, with significantly fewer steps than most known methods. Furthermore, contrary to the known methods of converting oleic acid to C11 nylon precursor, the reactions involved in the method herein are highly selective, thus avoiding the use of excessive reagents and thereby leading to fewer side products being formed. Moreover, energy-intensive high-temperature and high-pressure hydrogenation or pyrolysis reactions are avoided.

Figure 4:
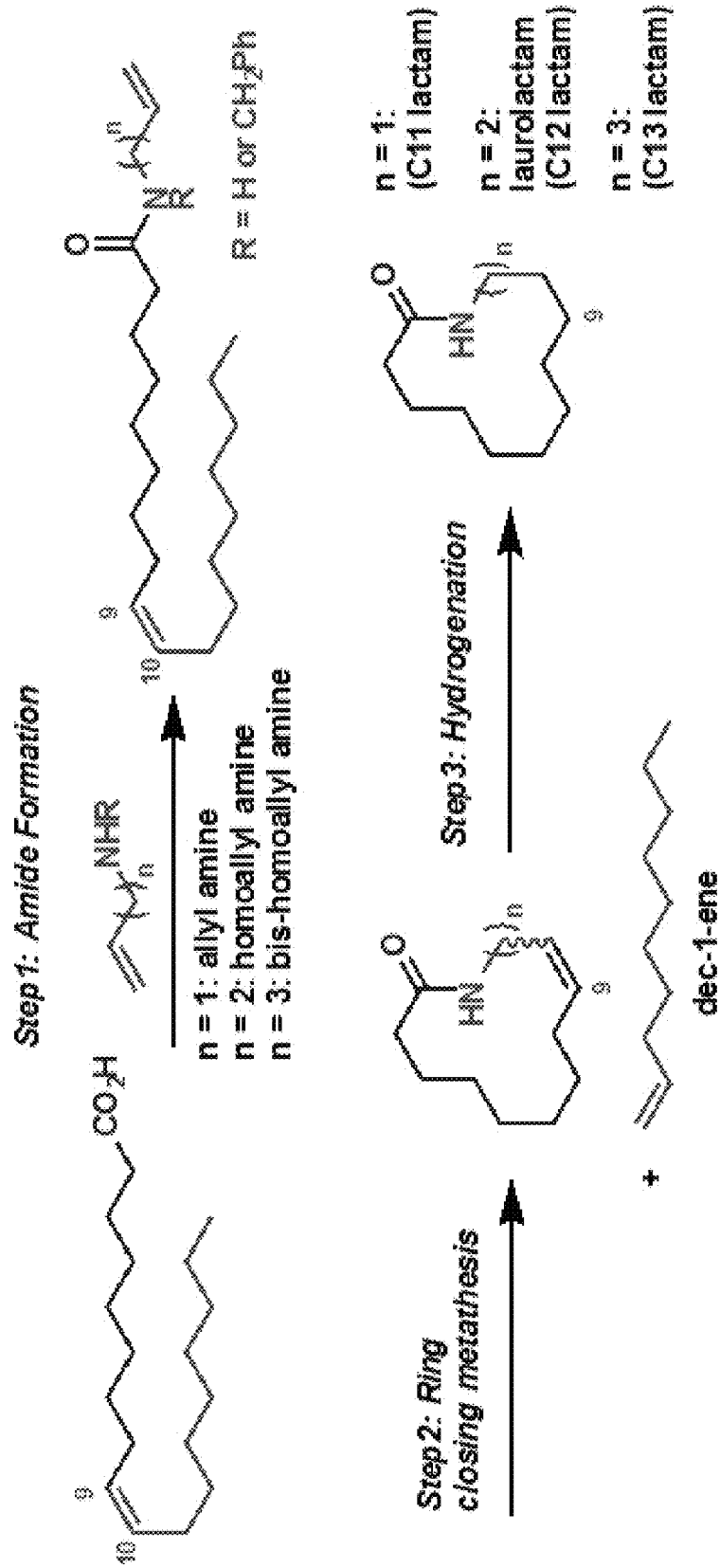
FIG. 4: Scheme showing a non-limiting example of the three-step method to produce C11, C12, and C13 lactams.

A non-limiting example of the three-step method for making lactams from oleic acid is illustrated in FIG. 4. In the first step, oleic acid (or an ester of oleic acid) is converted to allyl amide, homoallyl amide, or bis-homoallyl amide. The amide nitrogen can have another substituent, such as, but not limited to, benzyl, in order to facilitate the ring cyclization. The attachment of a substituent can be achieved either from amide by an alkylation of nitrogen, or from the acid by formation of amide with secondary amines. In certain examples herein, a benzyl substituent is described because it can be removed simultaneously in the third step. When other substituents are utilized, the method can involve an additional step of removing the substituent following hydrogenation.

The first step, amide formation, can be conducted in any suitable solvent. Non-limiting examples of suitable amidation solvents include, but are not limited to: chlorobenzene, triethylamine, toluene, dichloroethane, chloropentafluorobenzene, octafluorotoluene, $CH_2Cl_2$, MeOH, pentane, hexane, heptane, EtOAc, i-PrOAc, dimethyl carbonate, diethyl carbonate, HOAc, DMSO, DMF, pyridine, anisole, water, $Et_2O$, acetonitrile, hexafluorobenzene, or mixtures thereof. In particular embodiments, the amidation solvent comprises a mixture of triethylamine and dichloromethane.

Figure 3:
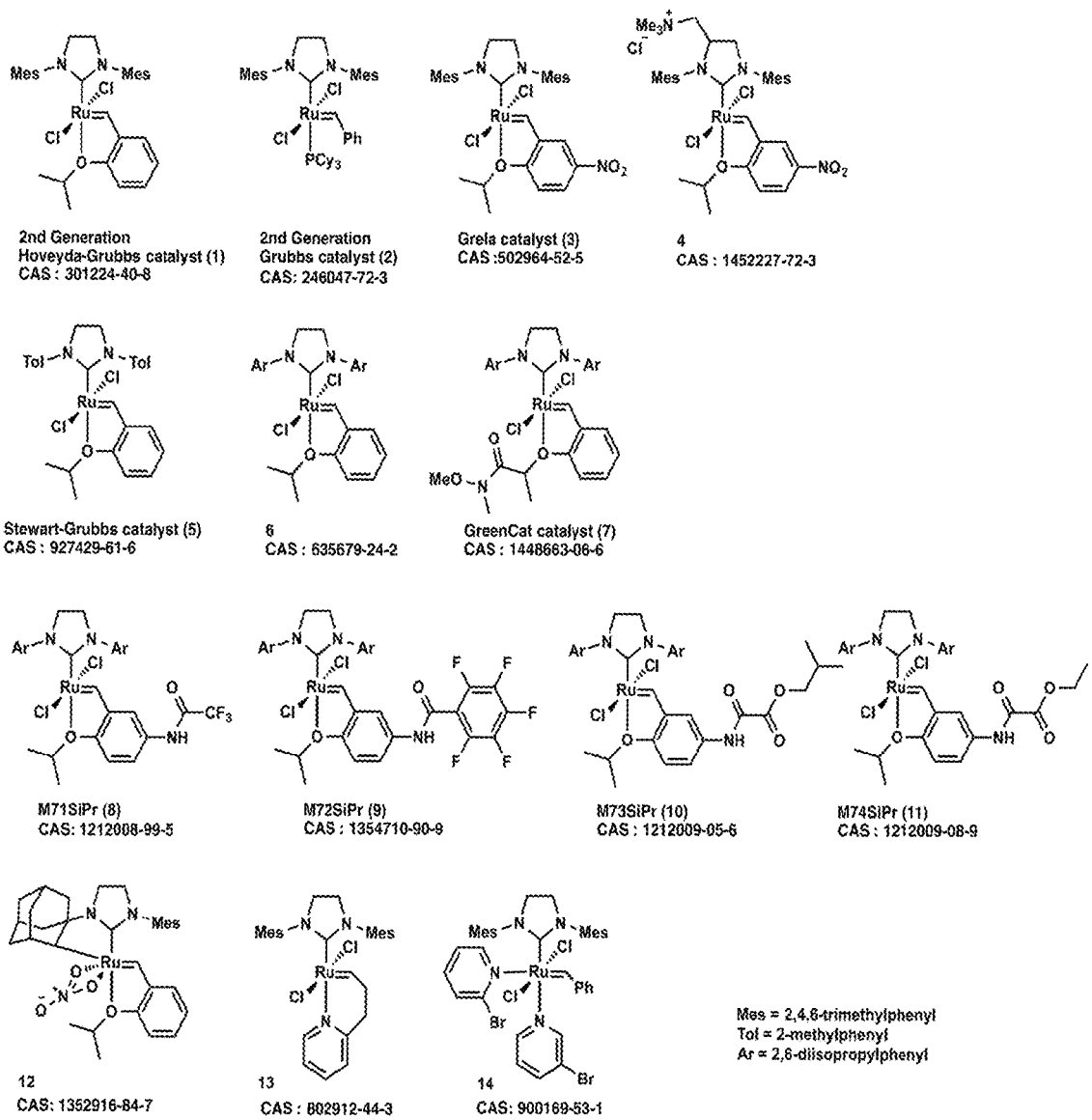
FIG. 3: Structures of non-limiting examples of suitable catalysts for a ring-closing metathesis reaction.

In the second step, a ring-closing metathesis reaction provides lactams having an olefin within the ring (ene-lactams). The ring-closing metathesis is generally performed in the presence of a metathesis catalyst. Any active suitable catalyst can be used as a metathesis catalyst. Some suitable metathesis catalysts are tungsten-, molybdenum-, and ruthenium-based complexes. These are homogenous catalysts, although heterogenous catalysts adsorbed on silica or alumina are also useful in certain embodiments. Additionally, immobilized catalysts, where the metal complex is attached to an inactive support through their ligands, can be used. In certain embodiments, immobilized catalysts are advantageous for purposes of catalyst recycling. By way of non-limiting examples, immobilization can be achieved utilizing soluble polymers, insoluble polymers, ionic liquids, monolithic gels, fluorous materials, or silica. Using an immobilized catalyst, a continuous process is possible. In some non-limiting examples, the catalyst is the commercially available Hoveyda-Grubbs catalyst (FIG. 3, complex 1); Umicore M73SiPr (FIG. 3, complex 10); or M74SiPr (FIG. 3, complex 11). Other possible catalysts include, but are not limited to, Group 8 transition metal complexes such as ruthenium or osmium alkylidene complexes substituted with an N-heterocyclic carbene ligand. Ruthenium and osmium carbene complexes having metal centers that are formally in the +2 oxidation state, having an electron count of 16, and that are penta-coordinated, are particularly useful catalysts for olefin metathesis reactions. Various first generation or second generation Grubbs-type catalysts can be used, such as a second generation Grubbs catalyst (FIG. 3, complex 2), or a second generation Hoveyda-Grubbs catalyst (FIG. 3, complex 1). In general, any of the complexes shown in FIG. 3 are suitable as a metathesis catalyst. The catalyst can be added to the reaction medium as a solid, or as a solution wherein the catalyst is dissolved in an appropriate solvent. It will be appreciated that the amount of catalyst that is used (i.e., the "catalyst loading") in the reaction is dependent upon a variety of factors such as the identity of the reactants and the reaction conditions that are employed. It is therefore understood that catalyst loading may be optimally and independently chosen for each reaction.

Many different metathesis solvents are possible. Suitable metathesis solvents can be polar or nonpolar and include, but are not limited to: chlorobenzene, toluene, dichloroethane, chloropentafluorobenzene, octafluorotoluene, $CH_2Cl_2$, anisole, MeOH, pentane, hexane, heptane, EtOAc, iPrOAc, dimethyl carbonate, diethyl carbonate, HOAc, DMSO, DMF, pyridine, water, $Et_2O$, acetonitrile, hexafluorobenzene, or mixtures thereof. In general, chlorinated and aromatic benzene derivatives, or fluorinated aromatic hydrocarbons, are suitable metathesis solvents. In particular embodiments, the metathesis solvent is chlorobenzene, ethyl acetate, or hexane.

The third step involves hydrogenation of the olefin as well as removal of the nitrogen substituent (if any), thereby providing the final product. Hydrogenation generally involves treating an unsaturated olefin with hydrogen in the presence of a hydrogenation catalyst to produce a saturated organic compound. However, hydrogenation can also be conducted in the absence of a catalyst at high temperatures. A number of suitable hydrogenation catalysts are palladium-based, typically adsorbed on a charcoal support. Suitable hydrogenation catalysts include those with a transition metal which forms one or more stable ions having incompletely filled d orbitals (i.e., Pd, Pt, Rh, Au, Ni, Co, Ru, or Ir). Noble metals, such as Pd, Pt, Rh, or Au, are especially suitable for this purpose. In these catalysts the transition metal can be supported, which means that the catalyst is dispersed on a second material that enhances the effectiveness. The support can be merely a surface on which the metal is spread to increase the surface area. Suitable supports are porous materials with a high surface area, such as alumina or various kinds of carbon. Further examples of supports include, but are not limited to, silicon dioxide, titanium dioxide, calcium carbonate, barium sulfate, diatomaceous earth, and clay. The metal itself can also act as a support, if no other support is present. Suitable hydrogenation catalysts of this type include, but are not limited to, a Raney catalyst (e.g. Ra—Ni, Ra—Co), Pd/C, Pd(OH)$_2$/C, Pd/CaCO$_3$, Pd/BaSO$_4$, Au/TiO$_2$, Rh/C, Ru/Al$_2$O$_3$, Ir/CaCO$_3$, or Pt/C. Optionally, organic hydride donor reagents such as diimide reagent can be used.

The hydrogenation catalyst can be homogenous (i.e., a catalyst that can be dissolved in the solvent containing the unsaturated substrated to be hydrogenated), or heterogeneous (i.e., a solid suspended in the solvent with the unsaturated substrated to be hydrogenated, or treated with gaseous substrate). Examples of homogenous catalysts include, but are not limited to, rhodium-based catalysts such as Wilkinson's catalyst, iridium-based catalysts such as Crabtree's catalyst, rhenium-based catalysts, or ruthenium-based catalysts. Examples of heterogenous catalysts include, but are not limited to, a Raney nickel or cobalt catalyst.

Some hydrogenation catalytic systems use phosphine ligands and a potassium tert-butoxide additive, and are carried out between 80-140° C. under 14-75 bar pressure hydrogen atmosphere. Milder reaction conditions can be utilized when the phosphine ligands of the complex are replaced with carbene ligands. In some embodiments, the hydrogenation is conducted at atmospheric pressure. Additionally, in certain embodiments the metathesis catalyst is used as the hydrogenation catalyst. Therefore, any first generation or second generation Grubbs-type catalyst, such as the complexes 1 or 2 (FIG. 3), can be used as the hydrogenation catalyst.

As with the ring-opening methasis step, many different solvents are possible for use in the hydrogenation step. Generally, the hydrogenation solvent is any of a number of alcohols, ethers, esters, aromatic hydrocarbons, aliphatic hydrocarbons, or combinations thereof. Suitable hydrogenation solvents include, but are not limited to: chlorobenzene, toluene, dichloroethane, chloropentafluorobenzene, octafluorotoluene, anisole, $CH_2Cl_2$, MeOH, HCl, pentane, hexane, heptane, HOAc, EtOAc, i-PrOAc, dimethyl carbonate, diethyl carbonate, DMSO, DMF, pyridine, water, $Et_2O$, acetonitrile, hexafluorobenzene, chloroform, cyclohexane, $Et_2O$, or mixtures thereof. In particular embodiments, the solvent is a mixture of MeOH with or without HCl.

When a substituent that is not removed simultaneously with the hydrogenation step is utilized, the method can involve an additional step of removing the substituent. Any suitable removal technique can be utilized for this purpose, and the optimal removal technique will depend on the identity of the substituent.

Figure 5:
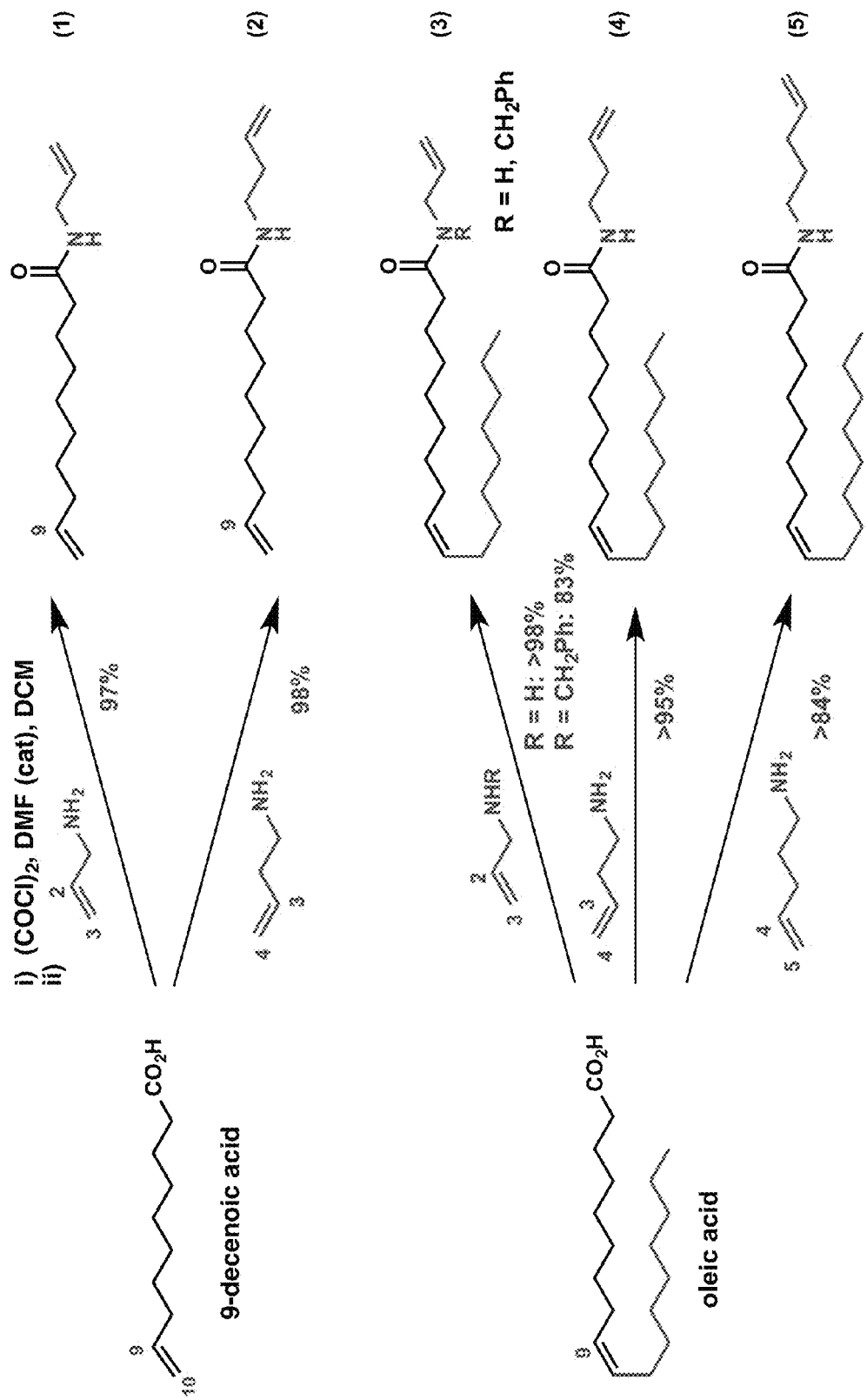
FIG. 5: Non-limiting example of step 1, amide formation of 9-decenoic acid and oleic acid.

The three-step method can be optimized. As a non-limiting example, an initial reaction optimization was performed using 9-decenoic acid as a model substrate of oleic acid. The first step, amide formation with corresponding amines, went smoothly under the conventional acid chloride formation, giving quantitative yields of the desired products. (FIG. 5, eq. 1-2.) The same reaction conditions were readily applied to oleic acid amides (FIG. 5, eq. 3-5), including the amide with a benzyl substituent.

Figure 6:
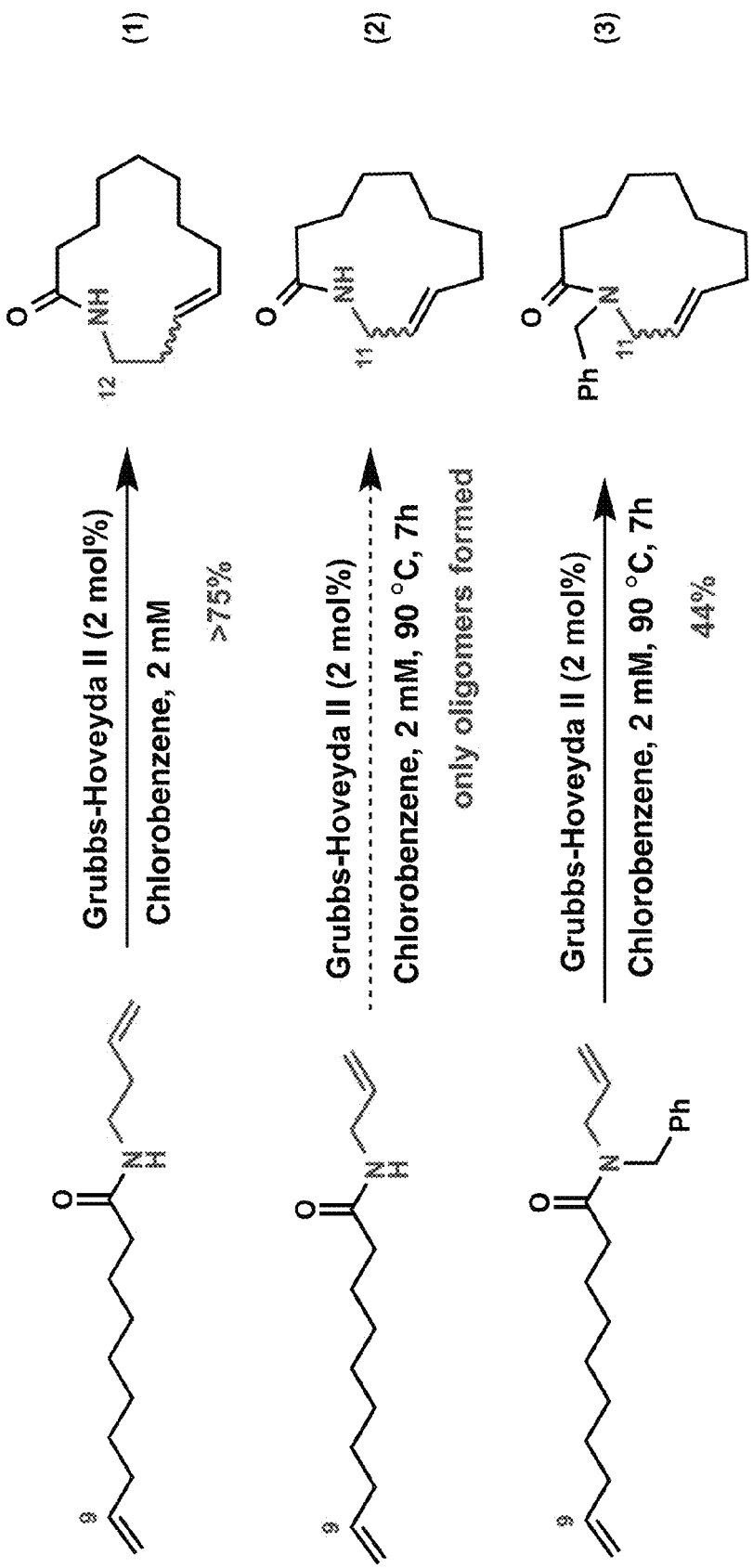
FIG. 6: Non-limiting example of step 2, ring-closing metathesis forming ene-lactams using model substrates (amides of 9-decenoic acid).

The ring-closing metathesis step was evaluated with the model substrates, amides prepared from 9-decenoic acid. (FIG. 6.) A ring-closing metathesis chemistry that forms 13-membered lactam uses an amide substrate with an olefin at a different position. Therefore, the same reaction conditions were examined using homoallyl 9-decenamide, the precursor for C12 ene-lactam. (FIG. 6, eq. 1.) Toluene was used instead of ionic liquid as a solvent, and the desired C12 lactam along with some oligomers were produced. A number of reaction parameters were screened in order to optimize the selectivity toward ring closure. (FIG. 9, Table 1.) The second generation Hoveyda-Grubbs catalyst (FIG. 3, complex 1) provided an especially desirable conversion, and drop-wise addition of the catalyst over one hour was used for the reaction to go to completion. Reaction temperatures between 80-100° C. were evaluated, and 90° C. gave optimal conversion and selectivity. (FIG. 9, Table 1, entries 4, 6, 12.) Minimally, 2 mol % of the catalyst was used in order to achieve a desired reaction conversion at this temperature. (FIG. 9, Table 1, entries 2, 7-8.) At higher temperatures, more catalyst was needed. Without wishing to be bound by theory, it is believed this was due to competing catalyst decomposition. (FIG. 9, Table 1, entries 11-12.)

The concentration of the reaction is an important parameter for any cyclization reaction. It was found that in order to obtain a good selectivity toward ring formation, a final concentration (after completion of catalyst addition) of at least 2 mM is most useful. (FIG. 9, Table 1, entries 3-4.) Other additives that may help catalyst decomposition (FIG. 9, Table 1, entries 9-10) or catalyst binding to the substrate (entry 13) were also examined, however no improvements were observed. Since solvent selection influences metathesis reactions, there are advantages to using halogenated solvents in metathesis. Surprisingly, it was found that replacing toluene with either chlorobenzene or anisole did not drastically change the reaction profile, though the number of impurities was reduced when chlorobenzene was used. (FIG. 9, Table 1, entries 4, 14-15.) Thus, the rest of the optimization was performed using chlorobenzene. Under the optimized reaction conditions (2 mol % Hoveyda-Grubbs catalyst, 1 h slow catalyst addition, 2 mM final concentration in chlorobenzene, at 90° C.), over 95% conversion was achieved after 2-2.5 h with formation of the desired lactams in 70-80% yield as ~3:1 geometric isomers for this reaction. (FIG. 6, eq. 1.)

Subjecting the allyl 9-decinamide, the precursor of C11 ene-lactam, to the same reaction conditions only produced isomerized starting materials as well as oligomerized products. (FIG. 6, eq. 2; FIG. 10, Table 2, entry 6.) Changing the reaction parameters such as concentration, catalyst loading, reaction temperature, and time did not improve the selectivity. (FIG. 10, Table 2, entries 1-6.) Without wishing to be bound by theory, it is believed that these results may be due to the higher ring strain of the desired product or stronger chelation of the catalyst to the allyl amide. However, addition of a Lewis acid that prevents catalyst binding to the substrate did not improve the selectivity in the system. (FIG. 10, Table 2, entry 7.) Since a substituent at the nitrogen of amide facilitates the s-cis conformation important for ring cyclization, this ring closing metathesis reaction was attempted using the substrate with a benzyl substituent. (FIG. 6, eq. 2.) The N-benzyl substrate was accessed from benzylation of the amide or by amide formation with allyl benzyl amine. The N-benzyl substrate provided improved selectivity and provided the desired cyclized product in approximately 34-44% yield by GC area. (FIG. 6, eq. 3; FIG. 10, Table 2, entries 8-9.)

Figure 7:
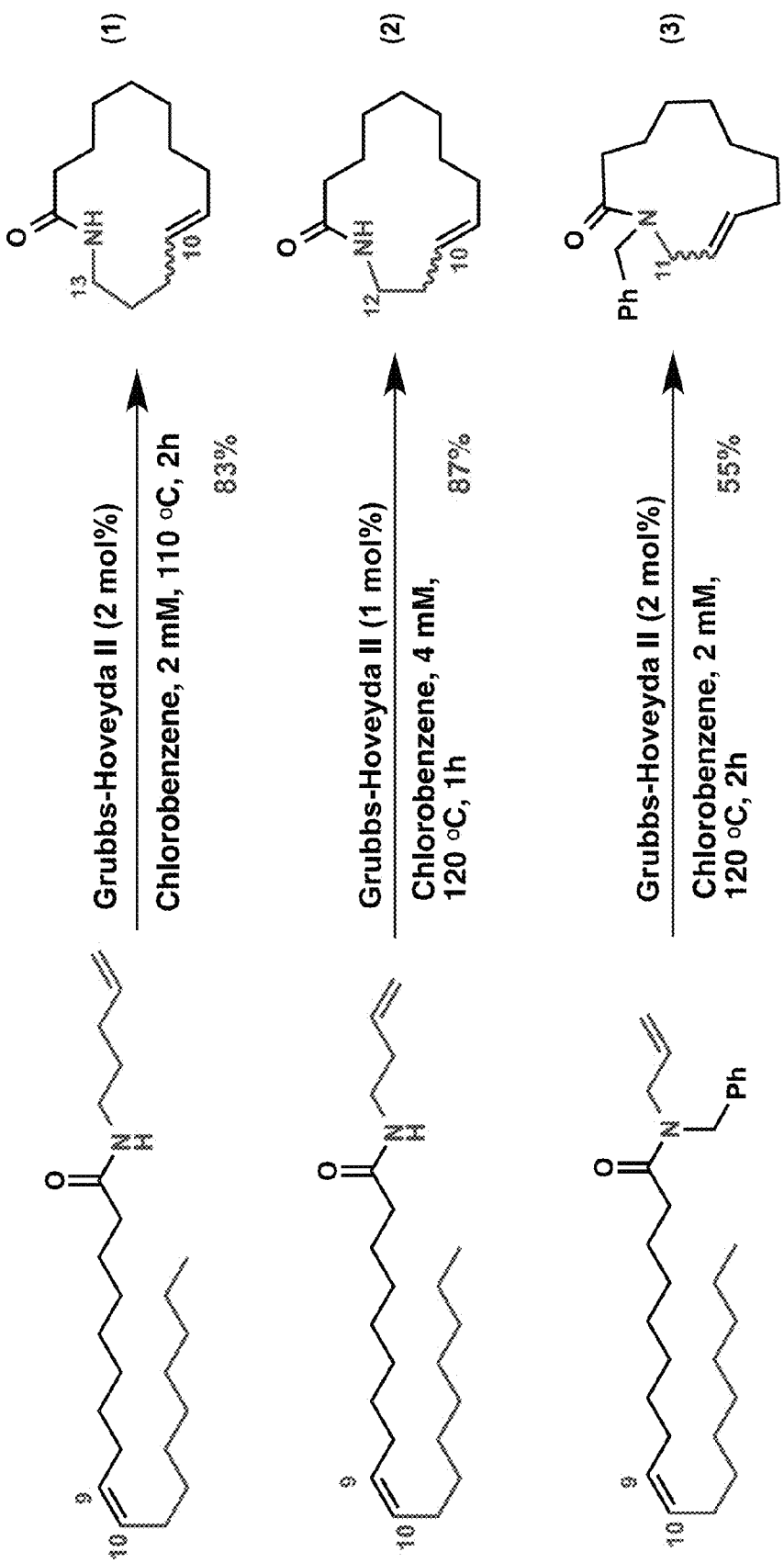
FIG. 7: Non-limiting example of step 2, ring-closing metathesis forming ene-lactams.

Next, the optimal reaction conditions were examined using the amide prepared from oleic acid. (FIG. 7.) Use of these amides, in general, provided better conversion and yield than the amides prepared from 9-decenoic acid. (FIG. 11, Table 3.) Without wishing to be bound by theory, it is believed that this trend is attributable to the lower reactivity of internal alkenes than terminal alkenes, which leads to better selectivity to cyclization products.

Fine-tuning of the reaction conditions can be beneficial. Reaction tuning for homoallyl amide ring-closing metathesis (for C12 ene-lactam formation) is shown in Table 3 (FIG. 11). With this substrate, slow catalyst addition was no longer necessary (FIG. 11, Table 3, entries 4, 7, and 11-14), catalyst loading was able to be reduced from 2 mol % to 1 mol % (entries 12-14), and the reaction temperature was able to be raised to 120° C., without affecting the conversion in shorter reaction times and while suppressing oligomerization (entries 9-11). However, reaction concentration needed to be retained (entries 4-6). Under these optimized conditions, C12 ene-lactam was obtained in 80-87% isolated yields. (FIG. 7, eq. 2.)

The above reaction conditions were applied to allyl amide of oleic acid (C11 ene-lactam formation). (FIG. 12, Table 4.) As with homoallyl amide, this substrate showed a better selectivity and conversion than the amide of 9-decenoic acid, as the substrate without a nitrogen substituent gave a small amount of the desired product. (FIG. 12, Table 4, entry 1.) The same reaction conditions were applicable to this substrate except it was determined that the catalyst should be added over 1 h and the catalyst loading should be greater than 2 mol % to achieve optimal results. With the substrate having nitrogen protection, the reaction provided about 50% of the C11 ene-lactam by GC area, which corresponded to 53-55% isolated yields. (FIG. 7, eq. 3; FIG. 12, Table 4, entries 2-4.)

Bis-homoallyl amide of oleic acid was subjected to the same reaction conditions. (FIG. 13, Table 5). This substrate behaved similarly to homoallyl amide, and gave a good conversion without much change to reaction conditions (FIG. 13, Table 5, entry 2), except it was determined that catalyst loading should be greater than 2 mol % (entries 1 and 3). Slow catalyst addition was found to be important (entries 1-2), and the optimal temperature was slightly lower at 110° C. (entries 1, 4-6). These reaction conditions provided C13 ene-lactam in 83% isolated yield. (FIG. 7, eq. 1; FIG. 13, Table 4, entry 1.)

With optimized reaction conditions in hand, a continuous process of this reaction that enables catalyst as well as solvent recycling was established. Development of such a process is important because of the high cost of the catalyst as well as the large volume of solvent required for this reaction. C12 lactam formation from homoallyl oleamide (FIG. 7, eq. 2) was first investigated because of its clean profile that does not require slow catalyst addition, indicative of a fast reaction that does not compete with a decomposition pathway. The successfully established process can be used as a template for developing processes for other metathesis reactions.

The catalyst stability under the optimized reaction conditions, 120° C. for 15 min in chlorobenzene at 2 mM substrate concentration, was tested (FIG. 11, Table 3, entry 13). In this experiment, a portion of the reaction mixture was taken for reaction monitoring, a fresh batch of substrate (N-(But-3-en-1-yl)oleamide) was added to the reaction mixture in 15 min intervals (the time required for reaction completion), and reaction conversion of each run was evaluated to assess the catalyst activity. With the above reaction conditions, however, the catalyst activity was lost after only the first reaction (conversion first: 98%; second: <15%).

Several previously reported procedures that immobilize second-generation Hoveyda-Grubbs catalyst onto various types of silica gel were also tested. Although there have been reports that demonstrated recovery and recycling of immobilized metathesis catalyst, when tested with the above reaction conditions and the substrate, it was found that all the catalyst was leached after the reaction (for details of the method, see example 9 below). Given that previous studies were performed under much milder reaction conditions at <80° C., other metathesis catalysts were investigated in order to find a more active catalyst that enables good conversion for this reaction without sacrificing its selectivity (FIG. 14, Table 6).

The metathesis catalysts that were investigated were selected based on either improved reactivity and/or stability tested against either ring-closing metathesis or cross-metathesis. There were no "bench-mark" reactions that had been being tested universally, and it was found that reported catalyst features were often not relevant to the system at hand. Nevertheless, several catalysts were found that performed better than second-generation Hoveryda-Grubbs catalyst (FIG. 3, complex 1), as shown in FIG. 14, Table 6. Prior to the catalyst screening, several alternative solvents were evaluated, and ethyl acetate was selected for further testing because of its cost and low toxicity.

For the ring-closing metathesis from homoallyl oleamide to C12 lactam, two trends can be drawn. First, as seen in the optimization (FIG. 11, Table 3), reaction at lower temperature resulted in increased oligomerization (FIG. 14, Table 6, entries 3 vs 4; 12 vs 13; 15 vs 16). Having known that catalyst immobilization was demonstrated for a reaction run at 80° C., it was determined that 60° C. would be a good balance between good selectivity while preventing catalyst decomposition. The second trend seen in the results was the time dependence of oligomer formation. It appeared that in many cases, C12 lactam formation superseded oligomer formation and the ratio between the two were the highest when the reaction was just about to complete, i.e., approximately 15 min for this reaction. When the reaction proceeded further, most tested reactions resulted in either similar (Table 6, entries 11-12, 14-15, 23-25) or increased (entries 2-3, 5-7, 17-19, 26-28) level of oligomers, which could be the result of interconversion between monomeric product and oligomer during the reaction. Overall, it was found that the two catalysts, Stewart-Grubbs catalyst (FIG. 3, complex 5) and M74SiPr (FIG. 3, complex 11), stood out among other catalysts with respect to reactivity and selectivity.

Next, the stability of the catalysts that had shown good conversion with reasonable selectivities was evaluated. This evaluation was performed with the procedure described above, except ethyl acetate was used as a solvent and the reaction temperature was kept at 60° C. (FIG. 15, Table 7). Most catalysts resulted in decreased reactivity in their third cycle. In this study, Umicore catalysts M73SiPr (10) and M74 SiPr (11) performed the best, with their reactivity retaining >70% in their fifth run. From this data, it was concluded that Umicore M74SiPr (11) was the best catalyst available from a reactivity, selectivity, and stability standpoint.

Finally, the catalytic activity of immobilized M74SiPr, and its retention, was tested (FIG. 14, Table 6, entries 29-31; example 9). The catalyst was immobilized non-covalently on silica gel. The reaction conversion was comparable to that of a homogenous system in either hexanes or ethyl acetate. The data showed that approximately 75% of the catalytic activity was retained when the recycled catalyst was used in hexanes solvent. These results indicate that this catalyst system is desirable for recycling and reuse when hexanes or other non-polar solvents are used.

Figure 8:
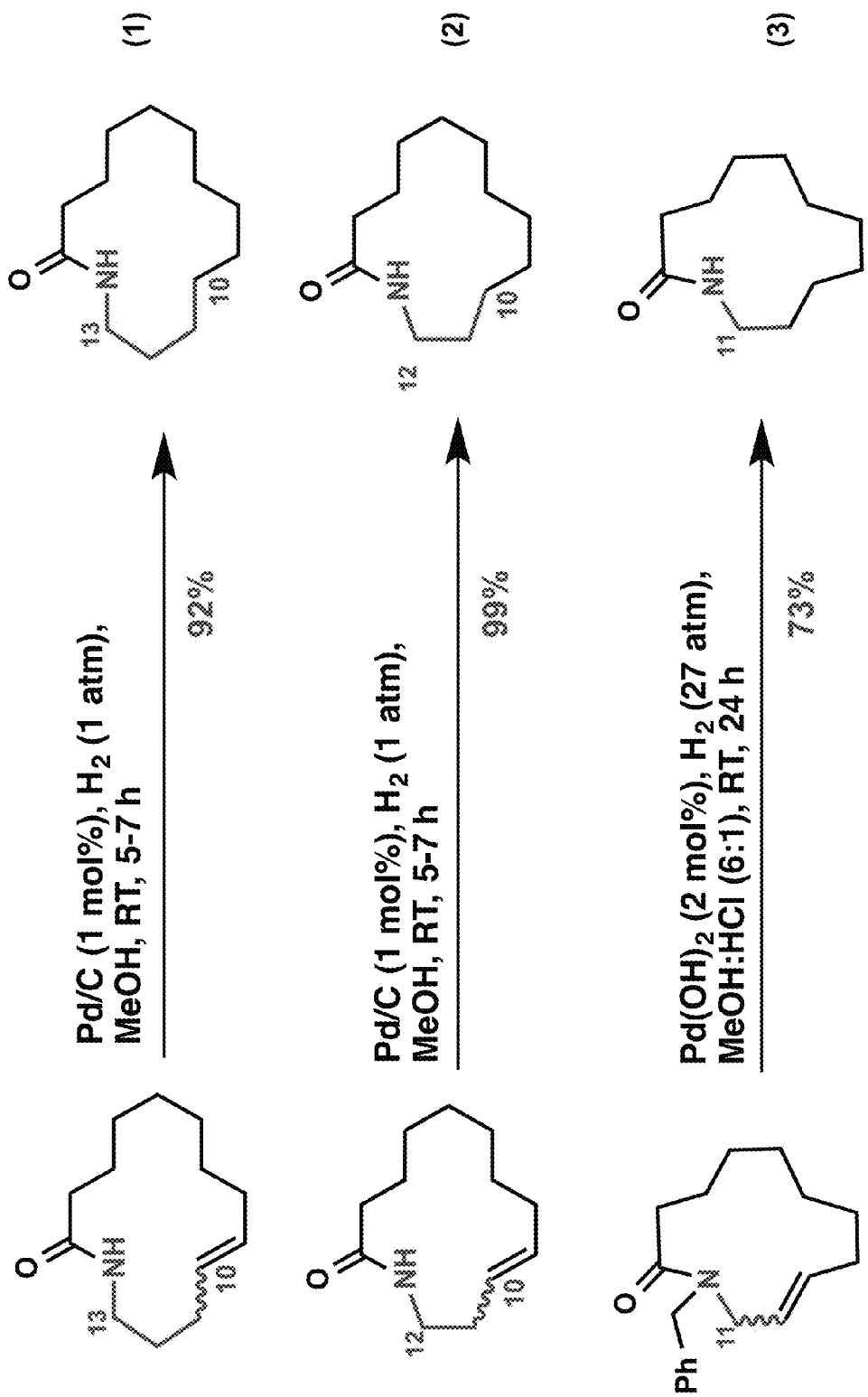
FIG. 8: Non-limiting example of step 3, hydrogenation forming C11, C12, and C13 lactams.

The hydrogenation of olefin was performed under the standard conditions providing greater than 90% of the final products. (FIG. 8, eq. 1-2.) The structure of C12 lactam, laurolactam, was confirmed by comparison of spectral data with that of the commercial product. Deprotection of the benzyl group of C11 lactam involved a high-pressure hydrogen atmosphere under acidic conditions as shown in the scheme in FIG. 8, eq. 3, and provided 73% yield of the final product.

The method of the present disclosure can be used to produce algae-based high-value nylons in an alternative to petroleum-derived products. The method can utilize microalgae feedstocks, which have a short growth cycle, higher surface productivity than terrestrial plants, high lipid content, and an ability to grow on wastewater systems. Microalgae is also less toxic than castor oil (which contains ricin). Nylons such as nylon 11, 12, and 13 possess excellent chemical resistance, good durability, flexibility, cold impact resistance, and thermal resistance. These products have many industrial applications in the automotive, sports, and medical industries, and are also useful for various products such as, but not limited to, high-performance cables, electronics, anti-termite cable sheathing, oil and gas flexible pipes, electrical compounds, sports shoes, catheters, control fluid umbilicals, pneumatic airbrake tubing, fuel lines, and lenses for glasses.

Nylon polymers can be produced from the nylon precursors generated from the method herein through any of several suitable methods. For nylon 12, the corresponding lactam (and not the linear amino acid or ester) is generally the precursor for polymerization used in manufacturing. Thus, the method provides a direct method to prepare the polymer precursors. Nylon 11, on the other hand, is currently produced by polymerization of linear C11 amino esters that can be readily accessed from C11 lactam by conventional solvolysis.

In certain embodiments, nylon polymers are produced from the saturated lactam nylon precursors generated from the three-step method through a ring-opening polymerization process. It is to be understood that any effective ring-opening polymerization process can be utilized to convert the saturated lactams made from the method herein into nylon polymers. By way of non-limiting examples, ring-opening polymerization of lactams can be achieved through the use of reagents including, but not limited to: strong ionic base catalysts comprising an alkali metal hydroxide together with an alkali metal, alkali metal amide, or alkali metal hydride; strong ionic base catalysts comprising an alkali metal or alkali metal hydride and alkaline earth metals or alkaline earth metal hydrides; phosphazene bases such as a $P_4$-phosphazene base; sodium lactonate salt catalysts; Grignard salts of ϵ-caprolactam; and N-heterocyclic carbenes. In one non-limiting example, a saturated lactam is contacted with an N-heterocyclic carbene-containing catalyst at a temperature ranging from about 190° C. to about 280° C. In certain embodiments, the lactam is placed in a mold prior to polymerization.

Alternatively, in certain embodiments, the saturated lactams can be subjected to ring-opening and polymerization in separate processes. The lactams can be subjected to ring-opening to form a linear nylon precursor, which is then polymerized into a nylon polymer. Various methods of lactam ring-opening are known in the art, and it is to be understood that any effective lactam ring-opening reaction can be used for this purpose. Non-limiting examples of ring-opening reactions include, but are not limited to: reacting the lactam with an amine in the presence of a monocarboxylic acid; contacting the lactam with a suitable enzyme; and treating the lactam with a primary or secondary amine in the presence of a suitable catalyst and cocatalyst. By way of non-limiting examples, either a batch autoclave (or discontinuous) method or a continuous polymerization (CP) method could be utilized to produce nylon polymers from the linear nylon precursors. In one non-limiting example of a conventional batch autoclave method, a 40-60% amino acid salt solution is charged into a pre-evaporator vessel operated at a temperature of about 130-160° C. and a pressure of about 240-690 kPa absolute, wherein the polyamide salt solution is concentrated to about 70-80%. This concentrated solution is transferred to the autoclave, where heating is continued as the pressure in the vessel rises to anywhere from about 1100 kPa to about 4000 kPa absolute. Steam is vented until the batch temperature reaches about 220-260° C. The pressure is then reduced slowly (over about 60-90 minutes) to less than about 100 kPa absolute. The polymer molecular weight is controlled by the hold time and pressure at this stage. Salt concentration, pressure, and temperature may vary depending on the specific polyamide being processed. After the desired hold time, the polyamide is then extruded into a strand, cooled, and cut into pellets (also known as granulates).

Continuous polymerization (CP) processes are also suitable methods of preparing nylons from the linear nylon precursors. In one non-limiting example of a continuous polymerization method, an amino acid (or polyamide) salt solution is preheated in a vessel to about 40-90° C. and transferred into a pre-evaporator/reactor, where the salt solution is concentrated at about 1350-2000 kPa absolute and about 200-260° C. to about 70-90%, resulting in a low molecular weight polymer. The low molecular weight polymer is then discharged into a flasher, where the pressure is slowly reduced to below about 100 kPa absolute and discharged into a vessel maintained below atmospheric pressure and at a temperature of about 270-300° C., to effect removal of water and to promote a further molecular weight increase. The polyamide melt is then extruded into a strand, cooled, and cut into pellets. Though a batch autoclave and CP method are described, the skilled person will recognize that any suitable method of preparing a nylon polymer is entirely within the scope of the present disclosure and can be readily utilized to prepare nylon polymers from the nylon precursors produced by the method described herein.

In any event, the resulting nylon polymers can be fabricated into articles of manufacture by a number of known techniques such as, but not limited to, extrusion, compression molding, and injection molding.

EXAMPLES

The synthesis of nylon 11, 12, and 13 lactam precursors from oleic acid in three steps is described in the following examples. It is to be understood that these examples are intended to be illustrative and non-limiting.

Example 1—Amide Formation with Oleic Acid and Benzyl Allyl Amine (FIG. 5, Eq. 3; R=$CH_2Ph$)

Oxalyl chloride (1.9 mL, 38.5 mmol) was added dropwise into a solution of oleic acid (2.40 g, 8.33 mmol) and DMF (70 µl, 0.89 mmol) in dichloromethane (20.0 mL) at 0° C. The mixture was warmed to room temperature and stirred for ~3 h, at which point the consumption of the starting material was seen by TLC. The reaction mixture was concentrated under reduced pressure and the residue was dissolved in dry dichloromethane (8.0 ml). The resulting solution was added dropwise into a solution of N-benzylprop-2-en-1-amine (0.955 g, 6.49 mmol) and triethylamine (5.0 mL, 36.0 mmol) in dichloromethane (20 mL) over 1 hour at 0° C. The mixture was brought to room temperature and stirred for 3 hrs. The reaction mixture was then neutralized with 2N HCl, washed with 5% $NaHCO_3$ (10 mL×3), saturated NaCl (10 mL×2), dried over anhydrous $MgSO_4$, filtered, and the solvent was evaporated under reduced pressure. The crude product was purified by column chromatography using hexane/ethylacetate (1/9, then 1:4, then 3:7) as eluent to provide the desired compound as a clear off-white viscous liquid (2.20 g, 82.5%).

Example 2—Amide Formation with Oleic Acid and Homoallyl Amine (FIG. 5, Eq. 4)

Oxalyl chloride (800 µl, 9 mmol) was added dropwise into a solution of oleic acid (1.01 g, 3.6 mmol) and DMF (30 µl, 0.4 mmol) in dichloromethane (10.0 mL) at 0° C. The mixture was warmed to room temperature and stirred for ~3 h, at which point the consumption of the starting material was seen by TLC. The reaction mixture was concentrated under reduced pressure and the residue was dissolved in dry dichloromethane (5.0 ml). The resulting solution was added dropwise into a solution of 3-butenylamine hydrochloride (540 mg, 5 mmol) and triethylamine (1.8 mL, 13 mmol) in dichloromethane (10 mL) over 30 min at 0° C. The mixture was brought to room temperature and stirred for 3 hrs. The reaction mixture was then neutralized with 2N HCl, washed with 5% $NaHCO_3$ (10 mL×3) and saturated NaCl (10 mL×3), dried over anhydrous $MgSO_4$, filtered, and the solvent was evaporated under reduced pressure. The crude product was purified by column chromatography using hexane/ethylacetate (1/3) as eluent to provide the desired compound as a white solid (1.10 g, 92%).

Example 3—Amide Formation with Oleic Acid and Bishomoallyl Amine (FIG. 5, Eq. 5)

Oxalyl chloride (800 µl, 9 mmol) was added dropwise into a solution of oleic acid (1.00 g, 3.6 mmol) and DMF (30 µl, 0.4 mmol) in dichloromethane (10.0 ml) at 0° C. The mixture was warmed to room temperature and stirred for ~2.5 h, at which point the consumption of the starting material was seen by TLC. The reaction mixture was concentrated under reduced pressure and the residue was dissolved in dry dichloromethane (5.0 mL). The resulting solution was added dropwise into a solution of pent-4-enylamine (350 mg, 4 mmol) and triethylamine (1.8 mL, 13 mmol) in dichloromethane (10 mL) over 30 min at 0° C. The mixture was brought to room temperature and stirred for 2 h. The reaction mixture was then neutralized with 2N HCl, washed with 5% $NaHCO_3$ (10 mL×3) and saturated NaCl (10 mL×3), dried over anhydrous $MgSO_4$, filtered, and the solvent was evaporated under reduced pressure. The crude product was purified by column chromatography using hexane/ethylacetate (1/4) as eluent to provide the desired compound as a white solid (1.04 g, 84%).

Example 4—Ring-Closing Metathesis with N-allyl-N-benzyloleamide (FIG. 7, Eq. 3)

N-allyl-N-benzyloleamide (25 mg, 98% pure by GC, 0.06 mmol) was dissolved in chlorobenzene (29 mL, $N_2$ purged for 20 min before use) and heated at 110° C. for 20 min Hoveyda-Grubbs $2^{nd}$ generation catalyst (0.8 mg, 0.0013 mmol) was dissolved in chlorobenzene (1 ml) and added dropwise to the reaction mixture over a duration of 1 hour. The solution was stirred under $N_2$ for another 1 h at this temperature. After being cooled to room temperature, the reaction mixture was passed through a short pad of silica gel to remove the catalyst. The column was flushed with a mixture of acetone/hexanes (3/7) and combined eluents were concentrated. The crude residue was purified by column chromatography using acetone/hexane (1/9) as the eluent to provide the desired cyclized product as a viscous liquid (8.9 mg, 52%).

Example 5—Ring-Closing Metathesis with Oleic Acid Homoallyl Amide (FIG. 7, Eq. 2)

N-(But-3-en-1-yl)oleamide (42.3 mg, 93% pure by GC, 0.12 mmol) was dissolved in chlorobenzene (30.5 mL, $N_2$ purged for 20 min before use) and heated at 120° C. for 20 min. Hoveyda-Grubbs $2^{nd}$ generation catalyst (0.8 mg, 0.0013 mmol) was dissolved in chlorobenzene (1 ml) and added to the reaction mixture. The solution was kept at this temperature for 1 h. After being cooled to room temperature, the reaction mixture was passed through a short pad of silica gel to remove the catalyst. The column was flushed with a mixture of ethyl acetate/hexanes (2/3) and combined eluents were concentrated. The crude residue was purified by column chromatography using acetone/hexane (1/9) as the eluent to provide the desired cyclized product as a white crystalline solid (20 mg, 87%).

Example 6—Ring-Closing Metathesis with Oleic Acid Bishomoallyl Amide (FIG. 7, Eq. 1)

N-(Pent-4-en-1-yl)oleamide (18 mg, 0.05 mmol) was dissolved in chlorobenzene (27 mL, $N_2$ purged for 20 min before use) and heated at 110° C. for 20 min Hoveyda-Grubbs $2^{nd}$ generation catalyst (0.7 mg) was dissolved in chlorobenzene (1 mL) and added drop wise to the amide solution via syringe over duration of 1 h. Heating at 120° C. was continued for additional 1 h. After being cooled to room temperature, the reaction mixture was passed through a short pad of silica gel to remove the catalyst. The column was flushed with a mixture of acetone/hexanes (2/3) and combined eluents were concentrated. The crude residue was purified by column chromatography using acetone/hexane (1/4) as the eluent to provide the desired cyclized product as a white crystalline solid (9 mg, 83%).

Example 7—Ring-Closing Metathesis with Oleic Acid Homoallyl Amide Using EtOAc Solvent (FIG. 14, Table 6, Entry 23)

N-(But-3-en-1-yl)oleamide (11.0 mg, 0.033 mmol) was dissolved in anhydrous ethyl acetate* (15 mL), without purging with nitrogen, and heated at 60° C. for 20 min Metathesis catalyst M74SiPr (1 mol %) was dissolved in anhydrous ethyl acetate (1 mL) and added to the reaction mixture. The solution was kept for 15 min at this temperature. After being cooled to room temperature, the reaction mixture was passed through a short pad of silica gel to remove the catalyst. The sample was analyzed by GC, which showed the desired C12 lactam as the major product in 72% yield by GC area.

*Note: Ethyl acetate used in this example was dried over molecular sieves for >24 h prior to use. Use of "wet" ethyl acetate with no treatment resulted in no reaction.

Example 8—Ring-Closing Metathesis with Oleic Acid Homoallyl Amide Using Hexanes Solvent (FIG. 14, Table 6, Entry 26)

N-(But-3-en-1-yl)oleamide (11.0 mg, 0.033 mmol) was dissolved in anhydrous hexane (15 mL), without purging with nitrogen, and heated at 60° C. for 20 min Metathesis catalyst M74SiPr (1 mol %) was dissolved in anhydrous hexane (1 mL) and added to the reaction mixture as a suspension. The solution was kept for 15 min at this temperature. After being cooled to room temperature, the reaction mixture was passed through a short pad of silica gel to remove the catalyst, and the sample was analyzed by GC, which showed the desired C12 lactam in 94.4% yield by GC area.

Example 9—Demonstration of Use of Silica Gel-Supported M74SiPr Catalyst (FIG. 14, Table 6, Entries 29-31)

M74SiPr catalyst was immobilized onto silica gel, and retention of the catalyst under the metathesis conditions were evaluated by the following method: the catalyst (immobilized on silica gel) was suspended in EtOAc or hexanes (15 mL) and warmed to 60° C. The substrate, N-(but-3-en-1-yl)oleamide (11.0 mg, 0.033 mmol) was dissolved in the solvent (EtOAc or hexanes, 1 mL) and was charged into the reaction slurry. After 15 min, the reaction solution was removed by a syringe and analyzed by GC (reaction conversion by GC area: EtOAc 97.6% (C12 lactam 76.9%); hexanes, 95% (C12 lactam 74.7%)). The silica gel remaining in the flask was subjected to the next reaction according to the same procedure to evaluate catalyst performance (reaction conversion by GC area: 71% (C12 lactam: 50.2%)).

Example 10—Hydrogenation of 1-benzylazacyclododec-10-en-2-one to Make C11 Lactam (FIG. 8, Eq. 3)

$Pd(OH)_2$ (20% wt. % on carbon, 50% wet, 2 mg) was added to a solution of 1-benzylazacyclododec-10-en-2-one (15 mg, 0.0552 mmol) in 1.0 ml of a mixture methanol: hydrochloric acid (6:1) at ambient temperature. The solution was stirred at 400 psi at ambient temperature for 24 hours, filtered through a Celite® bed, and the solvent was evaporated under reduced pressure. The crude was re-dissolved in 5 mL of dichloromethane, washed with 1 M NaOH (5 mL×2) and then with saturated NaCl (5 mL×2). The organic layer was dried with anhydrous $MgSO_4$ and filtered, and the solvent was evaporated under reduced pressure. The product was isolated as a white solid (~7.3 mg, 73%, corrected).

Example 11—Hydrogenation of Azacyclotridec-10-en-2-one to Make C12 Lactam (FIG. 8, Eq. 2)

10% Pd/C (50% wet) (1.5 mg, 0.0007 mmol), and azacyclotridec-10-en-2-one (14.2 mg, 0.07 mmol) in methanol (2 mL) were purged with hydrogen at room temperature at atmospheric pressure for 4 h. After completion of the reaction, the reaction mixture was passed through a Celite® bed to remove the catalyst. Solvent was evaporated using rotary evaporator to provide the product a white crystalline solid (14.1 mg, 99%, corrected).

Example 12—Hydrogenation of Azacyclotetradec-10-en-2-one to Make C13 Lactam (FIG. 8, Eq. 1)

10% Pd/C (50% wet) (1.3 mg, 0.0006 mmol), and azacyclotetradec-10-en-2-one (12 mg, 0.06 mmol) in methanol (2 mL) were purged with hydrogen at room temperature at atmospheric pressure for 4 h. After the reaction completion, the reaction mixture was passed through a Celite® bed to remove the catalyst. Solvent was evaporated using a rotary evaporator to provide the product as a white crystalline solid (11 mg, 98%, corrected).

Certain embodiments of the methods and products disclosed herein are defined in the above examples. It should be understood that these examples, while indicating particular embodiments of the invention, are given by way of illustration only. From the above discussion and these examples, one skilled in the art can ascertain the essential characteristics of this disclosure, and without departing from the spirit and scope thereof, can make various changes and modifications to adapt the compositions and methods described herein to various usages and conditions. Various changes may be made and equivalents may be substituted for elements thereof without departing from the essential scope of the disclosure. In addition, many modifications may be made to adapt a particular situation or material to the teachings of the disclosure without departing from the essential scope thereof.

What is claimed is:

1. A method for producing a lactam, the method comprising:
    converting oleic acid or an ester of oleic acid into an amide having a general formula of $H_3C-(CH_2)_7-CH=CH-(CH_2)_7-CONR-(CH_2)_n-CH=CH_2$, wherein n is 1, 2, or 3, and R is either hydrogen or benzyl;
    subjecting the amide to a ring-closing metathesis reaction to produce an intermediate having a general formula of $-(CH_2)-_7-CONR-(CH_2)_n-CH=CH_2-$, wherein n is 1, 2, or 3, R is either hydrogen or benzyl, and both ends are connected to each other; and
    hydrogenating the intermediate to produce a saturated lactam.

2. The method of claim 1, wherein the saturated lactam has a formula of $-NH-(CH_2)_{10}-CO-$, $-NH-(CH_2)_{11}-CO-$, or $-NH-(CH_2)_{12}-CO-$.

3. The method of claim 1, wherein the converting comprises subjecting the oleic acid or ester of oleic acid to an amide formation reaction with allyl amine, benzyl allyl amine, homoallyl amine, benzyl homoallyl amine, bishomoallyl amine, or benzyl bishomoallyl amine.

4. The method of claim 1, wherein the amide has a formula of $H_3C-(CH_2)_7-CH=CH-(CH_2)_7-CONH-(CH_2)_2-CH=CH_2$.

5. The method of claim 1, wherein the amide has a formula of $H_3C-(CH_2)_7-CH=CH-(CH_2)_7-CONR-CH_2-CH=CH_2$, wherein R is either hydrogen or benzyl.

6. The method of claim 1, wherein the amide has a formula of $H_3C-(CH_2)_7-CH=CH-(CH_2)_7-CONH-(CH_2)_3-CH=CH_2$.

7. The method of claim 1, wherein the converting is conducted in an amidation solvent selected from the group consisting of: chlorobenzene, triethylamine, toluene, dichloroethane, chloropentafluorobenzene, octafluorotoluene, $CH_2Cl_2$, MeOH, pentane, hexane, heptane, EtOAc, i-ProOAc, dimethyl carbonate, diethyl carbonate, HOAc, DMSO, DMF, pyridine, anisole, water, $Et_2O$, acetonitrile, hexafluorobenzene, and mixtures thereof.

8. The method of claim 1, wherein the intermediate has a formula of $-(CH_2)_7-CONH-(CH_2)_2-CH=CH_2-$.

9. The method of claim 1, wherein the intermediate has a formula of $-(CH_2)_7-CONR-CH_2-CH=CH_2-$, and R is either hydrogen or benzyl.

10. The method of claim 1, wherein the intermediate has a formula of $-(CH_2)_7-CONR-(CH_2)_2-CH=CH_2-$.

11. The method of claim 1, wherein the ring-closing metathesis reaction is conducted in the presence of a metathesis catalyst.

12. The method of claim 11, wherein the metathesis catalyst comprises a second generation Hoveyda-Grubbs catalyst, Stewart-Grubbs catalyst, or Umicore M74SiPr catalyst.

13. The method of claim 11, wherein the metathesis catalyst is attached to a solid support, the metathesis catalyst being capable of repeated use.

14. The method of claim 11, wherein at least one of the amide or the metathesis catalyst is dissolved in a metathesis solvent selected from the group consisting of: chlorobenzene, toluene, dichloroethane, chloropentafluorobenzene, octafluorotoluene, $CH_2Cl_2$, anisole, MeOH, pentane, hexane, heptane, EtOAc, i-PrOAc, dimethyl carbonate, diethyl carbonate, HOAc, DMSO, DMF, pyridine, water, $Et_2O$, acetonitrile, hexafluorobenzene, and mixtures thereof.

15. The method of claim 1, wherein the hydrogenation is conducted in the presence of a hydrogenation catalyst comprising a complex of Pd, Ru, or Ir.

16. The method of claim 15, wherein the hydrogenation reaction comprises dissolving the intermediate and the hydrogenation catalyst in a polar or non-polar hydrogenation solvent selected from the group consisting of chlorobenzene, toluene, dichloroethane, chloropentafluorobenzene, octafluorotoluene, ethyl acetate, isopropyl acetate, hexane, heptane, diethyl ether, MTBE, methanol, ethanol, and isopropanol.

17. The method of claim 1, wherein the hydrogenation is conducted at atmospheric pressure.

18. The method of claim 1, wherein the hydrogenation is conducted in the presence of an acid additive selected from the group consisting of mineral acids and Lewis acids.

19. The method of claim 1, wherein the oleic acid or ester of oleic acid is produced from storage lipids of algal biomass or from vegetable oil.

* * * * *